(12) United States Patent
Yamazaki et al.

(10) Patent No.: US 7,136,405 B2
(45) Date of Patent: Nov. 14, 2006

(54) LASER BEAM IRRADIATION DEVICE

(75) Inventors: Iwao Yamazaki, Tokyo (JP); Kimiyo Yamazaki, Tokyo (JP)

(73) Assignee: Ya-Man Ltd., Tokyo (JP)

( * ) Notice: Subject to any disclaimer, the term of this patent is extended or adjusted under 35 U.S.C. 154(b) by 0 days.

(21) Appl. No.: 10/490,999

(22) PCT Filed: Sep. 11, 2002

(86) PCT No.: PCT/JP02/09294

§ 371 (c)(1),
(2), (4) Date: Mar. 29, 2004

(87) PCT Pub. No.: WO03/028807

PCT Pub. Date: Apr. 10, 2003

(65) Prior Publication Data

US 2004/0243114 A1    Dec. 2, 2004

(30) Foreign Application Priority Data

Sep. 28, 2001    (JP)    ............................. 2001-303771

(51) Int. Cl.
*H01S 3/00*    (2006.01)
*A61B 18/18*    (2006.01)

(52) U.S. Cl. ............................... 372/38.09; 372/38.03; 372/38.01; 606/9

(58) Field of Classification Search ............... 372/38.1, 372/38.01, 38.02, 38.03, 43, 38.09; 606/9
See application file for complete search history.

(56) References Cited

FOREIGN PATENT DOCUMENTS

| JP | 07323093 | * 12/1995 |
|---|---|---|
| JP | 2001252363 | * 9/2001 |

* cited by examiner

*Primary Examiner*—Armando Rodriguez
(74) *Attorney, Agent, or Firm*—Bacon & Thomas

(57) ABSTRACT

A laser beam irradiation device is equipped with a very strict safety arrangement, thereby assuring that a user can use it safely. A hand-held applicator has a face formed on its top, and a push button switch on its side. The face has a spherical lens press-fitted in its center hole, and the face has a hollow cylinder integrally connected to its circumference, encircling the spherical lens. The hand-held applicator is applied to one's skin by the hollow cylinder at its edge. The hollow cylinder has a cylindrical electrode embedded in and somewhat projecting forward. A heat sink is placed behind the spherical lens, and a semiconductor laser diode is press-fitted in the through hole, which is made in the center of the heat sink. A cooling fan is placed behind the heat sink.

3 Claims, 6 Drawing Sheets

LASER BEAM IRRADIATION DEVICE

TECHNICAL FIELD

The present invention relates to a laser beam irradiation device for projecting a laser beam to one's skin for beauty treatments such as skin treatment, removal of undesired hair and suchlike to make persons more beautiful.

BACKGROUND ART

A laser beam is a very strong beam of controlled light whose energy density is much larger than that of a light beam from an ordinary light source, and therefore, exposure of a living body to the laser beam raises the temperature of an exposed spot high enough to injure or damage the spot by heat or transform its protein.

Especially, eyes, which are the light sensitive organs, can be incurably damaged, and so it is very dangerous to radiate the laser beam directly onto one's eye. The laser beam is a very strong beam of direction-controlled light so that the light power remains as high in the distance as it is at the light source or laser, and therefore, radiation of the laser beam onto an eye even from a remote light source is still hazardous to the eye.

Therefore, it is of a great concern that a beauty treatment laser device that is to be handled by a general user for skin treatment or removal of undesired hair be equipped with very strict safety means for preventing inadvertent projection of the laser beam to light-sensitive organs, such as eyes.

In view of this, one object of the present invention is to provide a laser beam irradiation device whose control circuit is equipped with foolproof safety means, thereby assuring that a general user can use the device with absolute safety.

SUMMARY OF THE INVENTION

To attain this object a laser beam irradiation device according to the present invention, comprises:

a hand-held applicator;

a semiconductor laser diode for radiating a laser beam;

a radiation switch for turning the laser diode on and off;

a touch sensor attached to the top of the hand-held applicator;

a standby switch for putting the device on standby condition for radiation;

an automatic switching arrangement responsive to expiration of a predetermined time subsequent to the turning-on of the standby switch for automatically turning the standby switch off; and a safety circuit responsive both to the touching of at least one portion of the touch sensor to the body and to the turning-on of the standby switch, and subsequent turning-on of the radiation switch for permitting a working current to flow in the semiconductor laser diode for radiating the laser beam.

The laser beam irradiation device is a device, using an electrically conductive cylinder as the touch sensor, the cylinder projecting forward from the front part of the top of the hand-held applicator.

The laser beam irradiation device is a device, using two electrically conductive rods as the touch sensor, the rods projecting forward from the front part of the top of the hand-held applicator.

DETAILED DESCRIPTION OF THE PREFERRED EMBODIMENT

The present invention is described below in respect of preferred embodiments.

Figure 1:
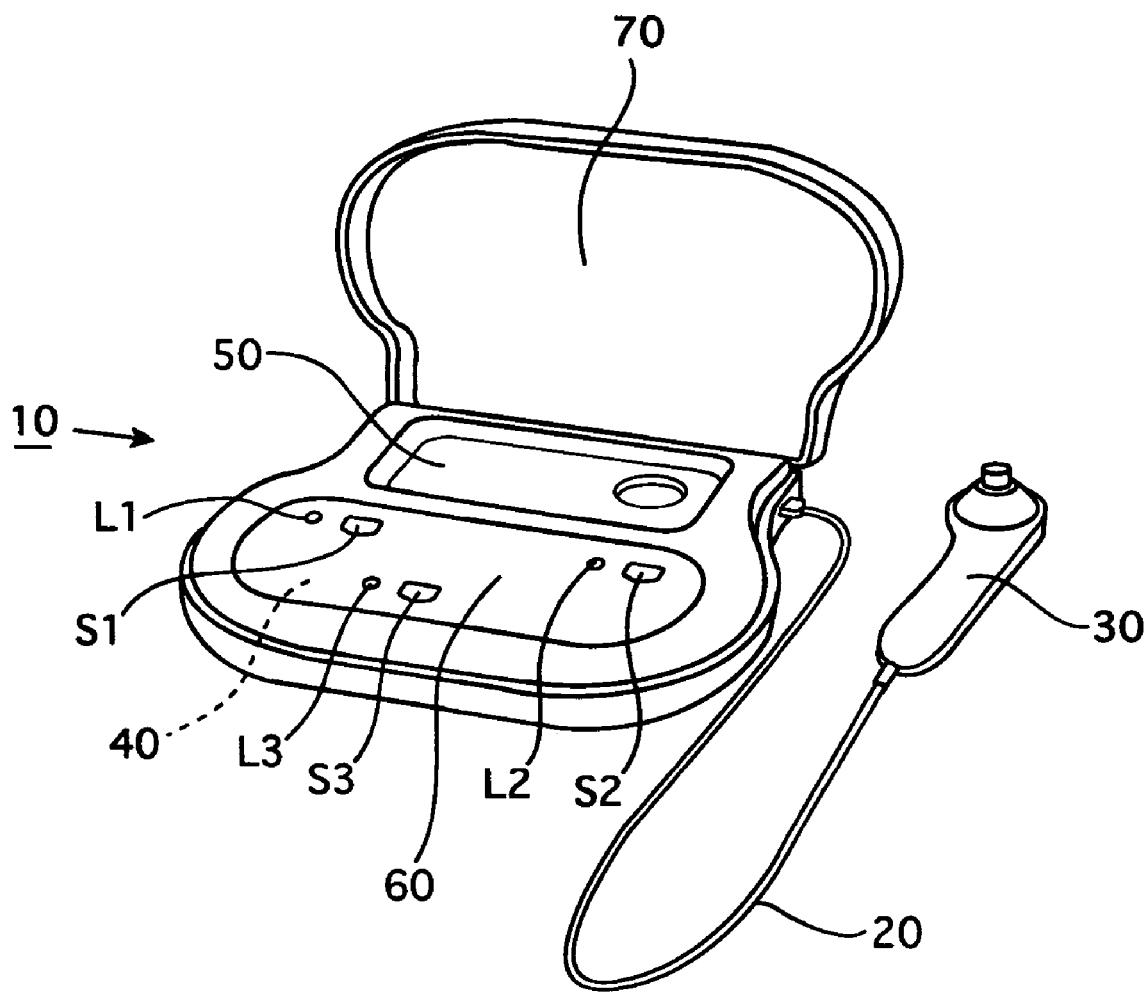
FIG. 1 is a perspective view of a laser beam irradiation device according to the present invention.

FIG. 1 shows how it looks in appearance.

The laser beam irradiation device comprises a major body 10 and an associated hand-held applicator 30 connected to the major body via a given length of cable 20.

The major body 10 contains a control circuit 40, and the housing of the major body 10 has a recessed compartment 50 for accommodating the hand-held applicator 30 and a console 60 on its top surface, and a lid 70 hinged to one side of the housing.

A power switch S1, a standby switch S2 and a radiation time setting switch S3 are arranged on the console 60.

Also, an LED power-on indicator lamp L1, a standby indicator lamp L2 and a six-step radiation time indicator lamp L3 are arranged next to the power switch S1, the standby switch S2 and the radiation time setting switch S3 on the console 60 respectively.

The six-level radiation time indicator lamp L3 comprises red and green LED chips in a single transparent enclosure. These LED chips are selectively or all together turned on to produce three different colored lights, namely, red, green and yellow or amber.

The power switch S1 when operated makes the power supply in the major body 10 turn on and off.

Accordingly the power-on indicator lamp L1 turns on and off.

When the standby switch S2 is turned on, the laser is set on a standby condition for radiation and the standby indicator lamp L2 turns on. When the standby switch S2 is turned off, the standby condition of the laser is cancelled and the standby indicator lamp L2 turns off.

The mere switching-on of the power switch S1 keeps the laser stay in non-standby condition.

When the standby switch S2 turns on, an associated timer starts counting to automatically turn off the standby switch S2 after a predetermined period (for example, 20 minutes) has passed irrespective of whether or not the laser has been radiated.

The radiation time setting switch S3 is responsive to each push for selectively setting a radiation dose of each shot in an intermittent radiation among the levels one to six.

The six-level radiation time indicator lamp L3 changes its light sequentially in the order of green, blinking green, amber, blinking amber, red and blinking red in response to the sequential change of the radiation dose from the levels one to six.

The radiation time setting switch S3 can be operated to set a desired radiation period even if the standby switch S2 is on.

The initial radiation dose is automatically set at the level one in response to the turning-on of the power switch S1.

The shot-to-shot interval in the intermittent radiation is determined (for example, 1.5 seconds) beforehand.

Figure 2:
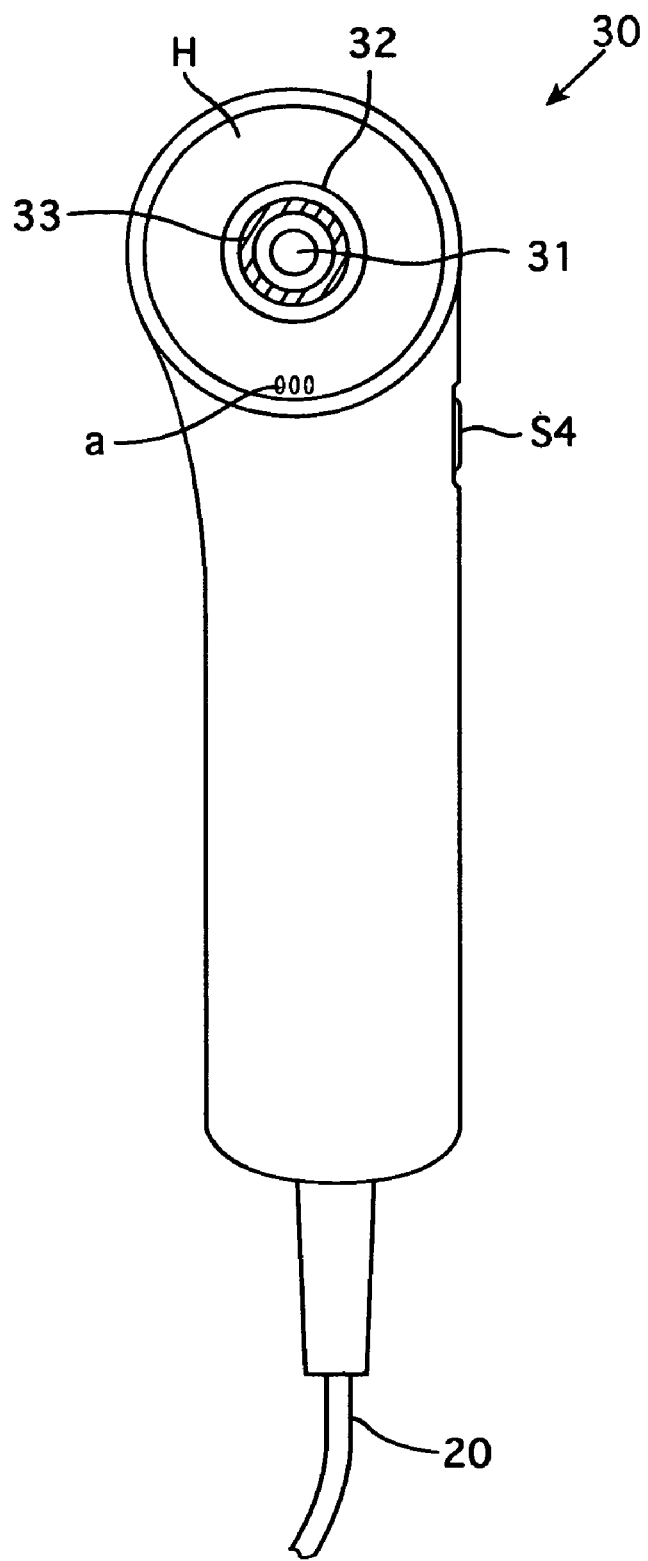
FIG. 2 is a front view of one example of the hand-held applicator
Figure 3:
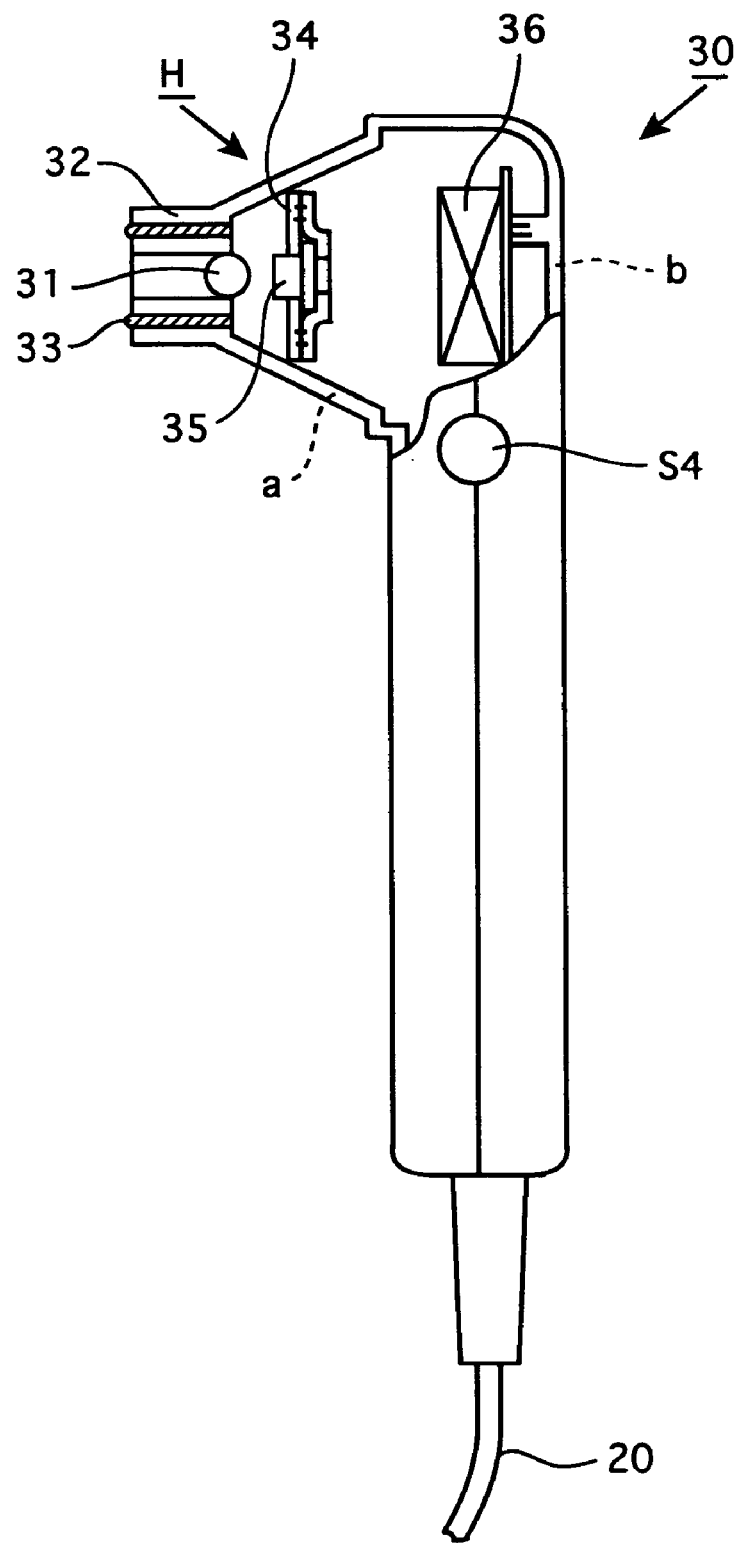
FIG. 3 is a side view of the hand-held applicator, partly in section.

Referring to FIGS. 2 and 3, the hand-held applicator 30 has a face H projecting laterally from its top, and a push button switch S4 on its side.

Also, the hand-held applicator has vent holes "a" and "b" at the lower part and on the rear side of the face H.

The face H has a spherical lens 31 press-fitted in its center hole, and the face H has a hollow cylinder 32 integrally connected to its circumference, encircling the spherical lens 31. The hand-held applicator 30 is applied to one's skin by the hollow cylinder 32 at its edge.

A coaxial cylindrical electrode 33 is embedded in the hollow cylinder 32 to project forward therefrom at its open edge.

A heat sink 34 is placed behind the spherical lens 31, and a semiconductor laser diode 35 is press-fitted in a through-hole bored in the center of the heat sink 34.

A cooling fan 36 is placed behind the heat sink 34.

The laser beam from the semiconductor laser diode 35 focuses on the focal point of the spherical lens 31 in the focal plane, in which the opening of the hollow cylinder 32 lies. The focal length of the spherical lens 31 is short enough to converge all the light energy to a limited spot, allowing the so converged beam to diverge beyond the focal point with the result that the light energy is distributed over the extensive area.

Accordingly the light energy density drastically decreases with the distance from the focal point, and therefore, there is little or no fear of injuring a living body even if it is exposed to the so dispersed light beam.

The heat sink 34 allows the heat generated by the semiconductor laser diode 35 to transmit therethrough. Thus, the semiconductor laser diode 35 is prevented from lowering its output.

The heat sink 34 is made of aluminum or aluminum alloy, whose thermal conduction is relatively high, and the heat sink 34 has further through holes made therein to effectively improve its heat radiation.

The semiconductor laser diode 35 may be a PN junction diode of GaAs or any other compound semiconductor, which can be excited by making an electric current flow therethrough for laser oscillation.

The peak-to-peak wavelength of the semiconductor laser diode is 600 to 1600 nm long, and the laser output ranges from 5 mW to 3W, thereby efficiently causing a sufficient photothermal reaction on the skin.

Further caused are additional optical effects other than the required photothermal reaction, such as photoelectric effect, photo-magneto effect, photo-dynamics effect, photochemical effect, photo-immunizing effect, photo-zymogenesis effect and the like. The photo-biological activation expedites the body's metabolism and blood circulation under the skin. The laser beam is hardly absorbed by the water contents and blood, and therefore, it can reach deep under the skin.

Figure 4:
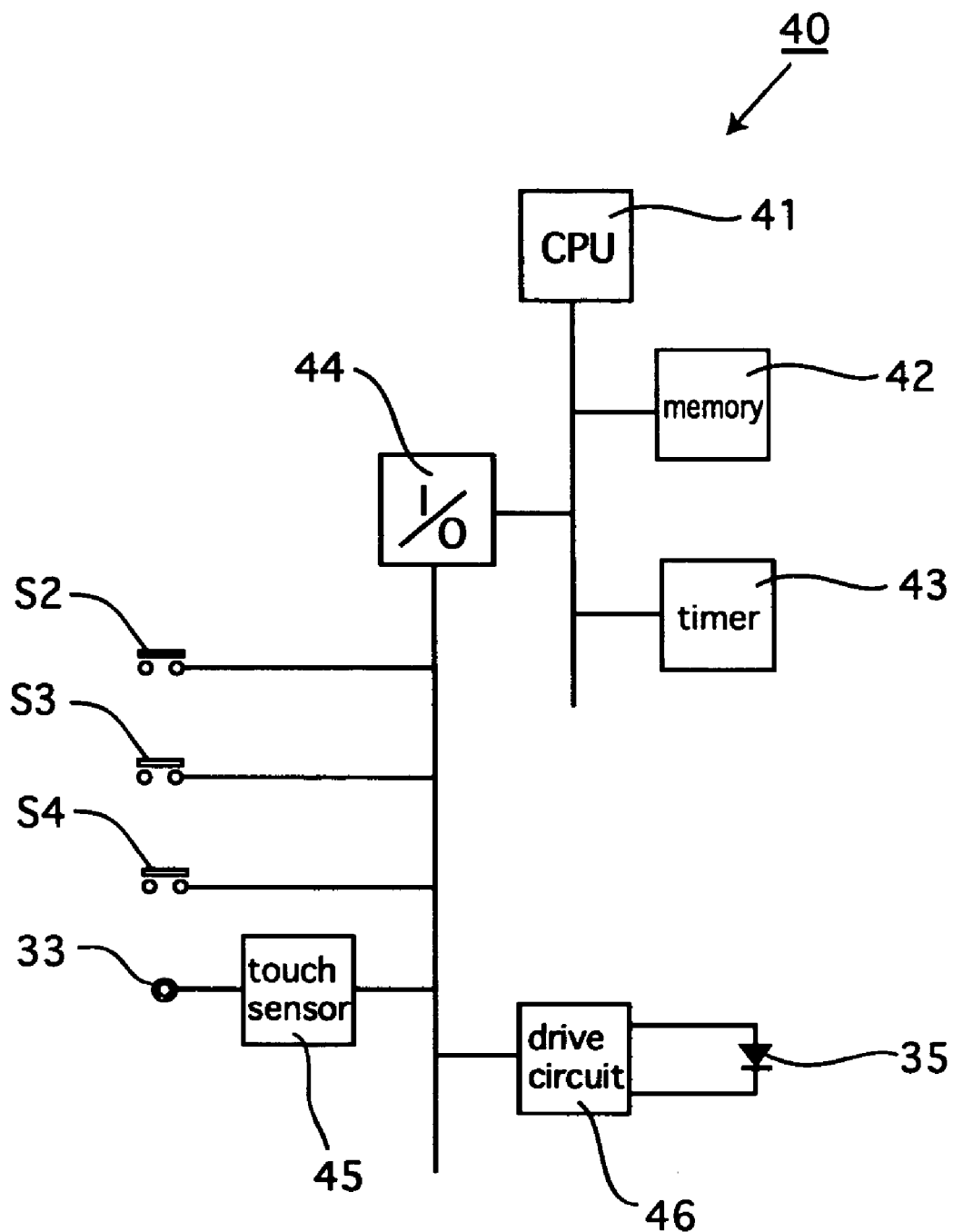
FIG. 4 is a block diagram of the control circuit.

FIG. 4 shows the control circuit of the laser beam irradiation device.

It comprises: a CPU 41 having a memory 42 and a timer circuit 43 both built therein; a standby switch S2, a radiation time setting switch S3, a push button switch S4 and a touch sensor circuit 45 for detecting the touching of the electrode 33 on the skin, of which all the switches and touch sensor circuit being connected on the input side of an I/O port 44; and a drive circuit 46 connected on the output side of the I/O port 44 for controlling the working current in the semiconductor laser diode 35.

The touch sensor circuit 45 comprises a high-frequency oscillator circuit and a switching circuit responsive to the working or non-working of the oscillator for turning on or off.

The electrode 33 is connected to one terminal of an oscillation coil of the oscillator circuit, and the oscillation stops as the electrode 33 touches the skin. The switching circuit is responsive to the stop of the oscillation for turning off.

The touch sensor circuit 45 may include an impedance element such as a capacitance or a resistance whose impedance drastically varies in response to the touching of the electrode to the skin, or may include a switching element or a piezoelectric element responsive to the touching of the electrode to the skin.

The CPU 41 carries out the on-and-off control of the working current from the drive circuit 46 under the control of the timer circuit 43.

The timer control includes two different modes, that is, the treatment time control in which the working current is made to flow a predetermined length of time for each treatment, and the radiation dose control in which the working current is made to flow a predetermine length of time for each shot in the intermittent radiation.

The length of time for a single dose can be set by the radiation time setting switch S3.

In carrying out a required beauty treatment with the so constructed laser beam irradiation device of the present invention, first the power switch S1 is turned on.

Then, the radiation setting switch S3 is kept being pushed until an indication representing a required length of time for radiation appears. When the indication appears, the switch S3 is released, thus setting the time for a single dose.

Next, the standby switch S2 is turned on to put the device in the standby condition.

The hand-held applicator 30 is held in hand with the face H directed towards a selected spot on the skin at the angle of 90 degrees relative to the skin, and then, the electrode 33 of the cylinder 32 is pushed against the selected spot.

Then, the push button switch S4 is depressed to turn on the semiconductor laser diode 35 for predetermined seconds, and then turns off for prescribed seconds.

The semiconductor laser diode 35 turns on or off alternately, thus, the skin is exposed to the intermittent radiation of laser beam.

A required beauty treatment is repeated as many times as required while moving the electrode 33 of the hand-held applicator 30 from place to place on the skin.

The radiation of the laser beam is made to stop in response to the electrode 33 being taken off from the skin, and the radiation of the laser beam is made to start in response to the electrode 33 being put on the skin.

Assuming that a fixed length of time has passed since the turning-on of the standby switch S2, it automatically turns off, thereby stopping the radiation of the laser beam.

Figure 5:
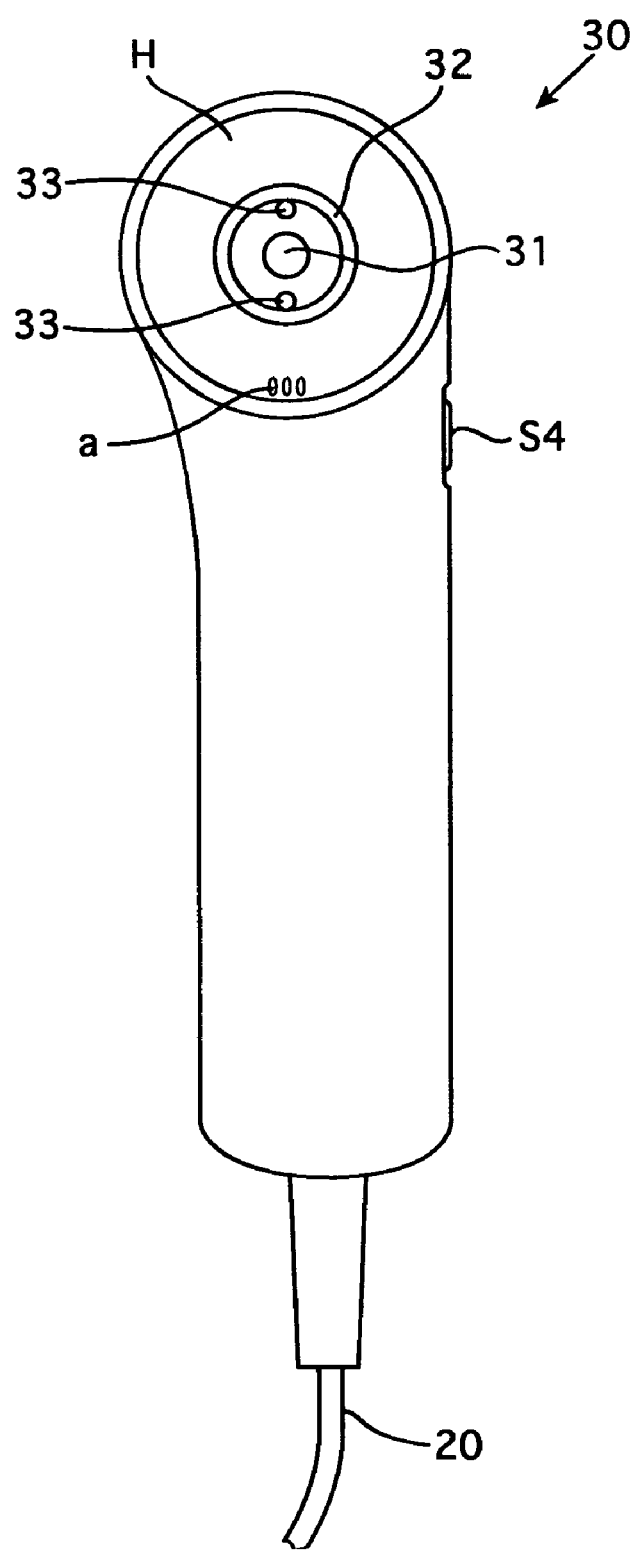
FIG. 5 is a front view of another example of hand-held applicator.
Figure 6:
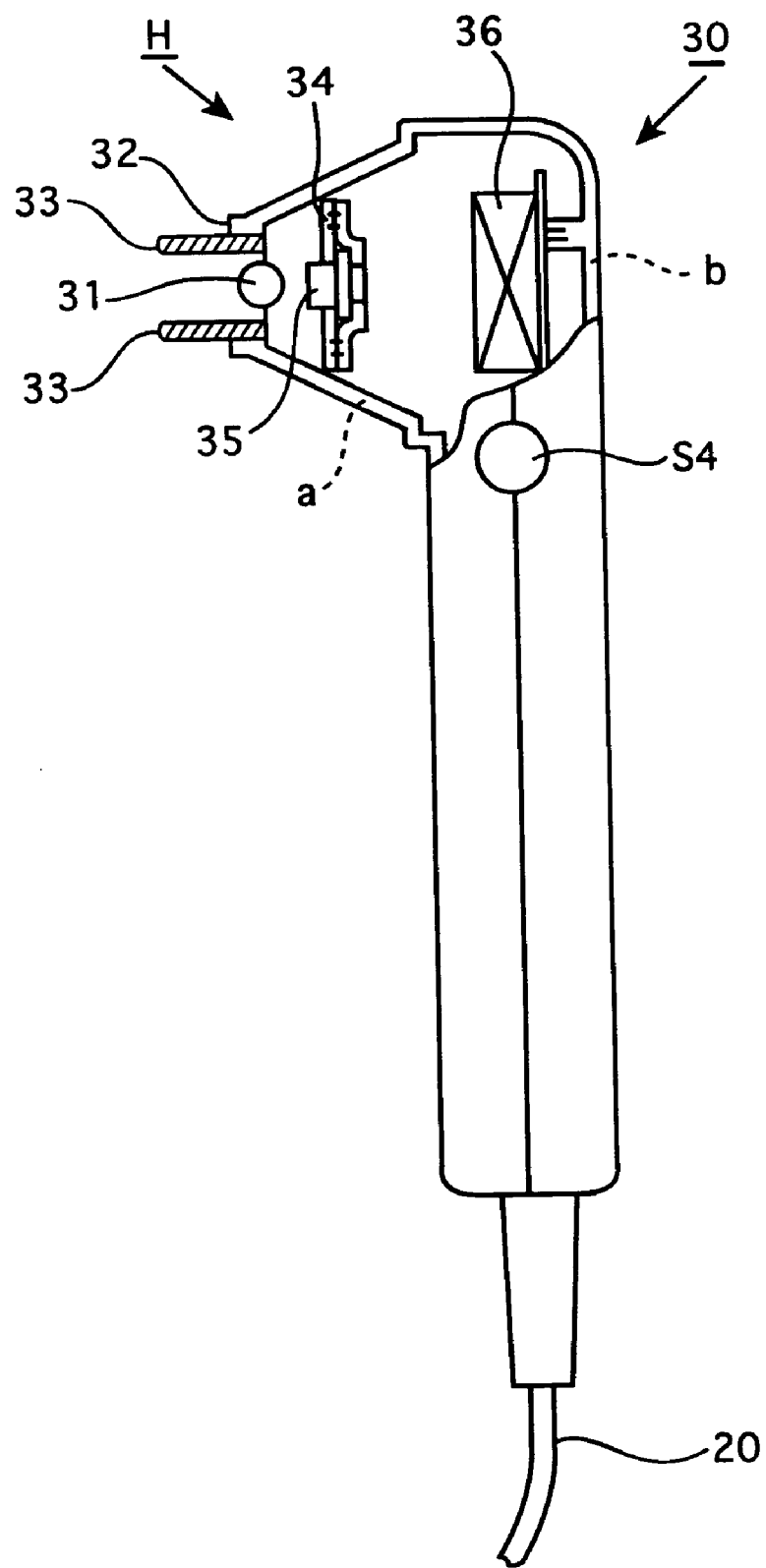
FIG. 6 is a side view of the hand-held applicator of FIG. 5, partly in section.

FIGS. 5 and 6 are front and side views of the hand-held applicator 30 having two rod-like electrodes 33 on its face front.

As shown in the drawings, two rod-like electrodes 33 stand upright on the face front ahead of the spherical lens 31, which is placed in the center of the face H.

The rod-like electrodes 33 are of electrically conductive metal, and their ends may be rounded or flattened. They may be gold-plated.

Three or more rod-like electrodes may be used. Depression of the push button switch S4 causes radiation of the laser beam, provided that any one or more of the rods 33 be put in contact with the skin.

INDUSTRIAL APPLICABILITY

As described above, the laser beam irradiation device of the present invention is responsive to the touching of at least a part of the touch sensor onto the skin for making a working current flow in the semiconductor laser diode for radiation, provided that the standby switch is on, and that the radiation switch turns on.

Therefore, erroneous depression of the radiation switch prior to the touching of the face of the hand-held applicator onto the skin does not permit radiation of the laser beam, assuring that the laser beam irradiation device be used safely.

Removal of the hand-held applicator apart from the skin makes the laser beam automatically stops, thereby preventing any danger of miss-radiation that may be caused by inadvertent removal of the hand-held applicator from the skin.

The laser beam cannot be radiated without turning the standby switch on, thus assuring that radiation of the laser beam cannot be caused except for the beauty treatment being carried out.

On the expiration of a predetermined time subsequent to the turning-on of the standby switch the automatic switching means makes the standby switch turn off, thus preventing the laser beam from radiating any longer.

The touch sensor as in the present invention is given in the form of an electrically conductive cylinder or two or more electrically conductive rods, somewhat projecting ahead of the face front.

This arrangement makes it unnecessary to keep the face front of the hand-held applicator pushed flat against the skin surface during the beauty treatment, thereby facilitating application of the hand-held applicator onto the skin. Accordingly the hand-held applicator can be handled smoothly.

The invention claimed is:

1. A laser beam irradiation device, comprising:
   a hand-held applicator;
   a semiconductor laser diode for radiating a laser beam;
   a radiation switch for turning said laser diode on and off;
   a touch sensor attached to the top of said hand-held applicator;
   a standby switch for putting the laser beam irradiation device on standby condition for radiation;
   an automatic switching means responsive to expiration of a predetermined time subsequent to the turning-on of said standby switch for automatically turning said standby switch off; and
   a safety circuit responsive both to the touching of at least one portion of said touch sensor to the body and to the turning-on of said standby switch, and subsequent turning-on of said radiation switch for permitting a working current to flow in said semiconductor laser diode for radiating the laser beam.

2. A laser beam irradiation device according to claim 1, wherein: said touch sensor comprises an electrically conductive cylinder, said electrically conductive cylinder projecting forward from the front part of the top of said hand-held applicator.

3. A laser beam irradiation device according to claim 1, wherein: said touch sensor comprises two electrically conductive rods, said two electrically conductive rods projecting forward from the front part of the top of said hand-held applicator.

* * * * *